United States Patent [19]
Bloch

[11] 3,931,272
[45] Jan. 6, 1976

[54] BIODEGRADABLE DETERGENTS
[75] Inventor: Herman S. Bloch, Skokie, Ill.
[73] Assignee: Universal Oil Products Company, Des Plaines, Ill.
[22] Filed: Dec. 4, 1974
[21] Appl. No.: 529,319

Related U.S. Application Data
[63] Continuation-in-part of Ser. No. 277,837, Aug. 3, 1972, Pat. No. 3,867,432.

[52] U.S. Cl. ................................................. 260/458
[51] Int. Cl.$^2$...................................... C07C 141/10
[58] Field of Search ................................. 260/458 C

[56] References Cited
UNITED STATES PATENTS
3,332,978  7/1967  Caldwell ........................ 260/458 C
3,652,684  3/1972  Schmerling et al. ............ 260/617 R Primary Examiner—James O. Thomas, Jr.
Assistant Examiner—Nicky Chan
Attorney, Agent, or Firm—James R. Hoatson, Jr.; Raymond H. Nelson; William H. Page, II

[57] ABSTRACT

Novel compositions of matter which are useful as biodegradable detergents comprise alkali metal disubstituted cyclohexenyl sulfates. These compounds are prepared by condensing butadiene with allyl chloride, thereafter ring alkylating the resultant chloromethylcyclohexene with an olefin in the presence of a free-radical generating compound and reacting the disubstituted cyclohexene with an alkali metal salt of a sulfur-containing compound to form the desired product.

6 Claims, No Drawings

BIODEGRADABLE DETERGENTS

CROSS-REFERENCE TO RELATED APPLICATIONS

This application is a continuation-in-part of my copending application Ser. No. 277,837 filed Aug. 3, 1972, now U.S. Pat. No. 3,867,432, all teachings of which are specifically incorporated herein by reference thereto.

This invention relates to novel compositions of matter and also to a process for preparing these compounds which are useful as biodegradable detergents. More specifically, the invention is concerned with these compounds comprising alkali metal salts of disubstituted cyclohexene sulfates which are biodegradable in nature when formed.

One of the major problems which is prevalent in population centers throughout the world is the disposal of sewage containing detergents dissolved therein. Such disposal problems are especially trying in the case of branched chained alkylaryl detergents. These detergents produce stable foams in hard or soft waters in such large quantities that the foam clogs sewage treatment facilities, and destroys the bacteria which are necessary for proper sewage treatment. In many rivers, streams, lakes, etc., which act as a water supply for the aforesaid population centers, there are found these unwanted foams and suds. As hereinbefore set forth, the presence of these unwanted foams or suds is due in many instances to the use of detergents which are non-biodegradable in nature and which will not break down by bacterial action thereon. The non-biodegradable nature of these detergents is due to the fact that the alkyl side chain of the molecule is in many instances highly branched and therefore not readily attacked by the organisms which would ordinarily destroy the molecule. In contradistinction to this, the use of straight chain alkyl substituents on the ring will permit the detergents to be destroyed and therefore foams or suds will not build up on the surface of the water.

It is therefore an object of this invention to provide a novel method for the manufacture of biodegradable detergents which may be degraded in both urban and rural sewage disposal systems.

A further object of this invention is to provide novel compositions of matter comprising biodegradable detergents.

In one aspect an embodiment of this invention resides in a biodegradable detergent compound of the formula:

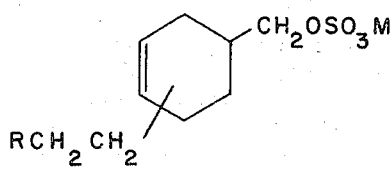

in which M is an alkali metal and R is an alkyl group of from 1 to about 14 carbon atoms.

A specific embodiment of this invention is found in a biodegradable detergent such as sodium(n-octyl-3-cyclohexenyl)methano sulfate.

Other objects and embodiments will be found in the following further detailed description of the present invention.

As hereinbefore set forth, the present invention is concerned with novel compositions of matter and to a process for the preparation of these compounds which are useful as biodegradable detergents, the process being effected in a series of steps. In the first step of the reaction, butadiene is reacted with allyl chloride in a Diels-Alder type condensation to give 4-chloromethylcyclohexene. Homologs of butadiene, such as isoprene, or analogous cyclic conjugated dienes such as cyclopentadiene or cyclohexadiene may be used instead of butadiene, and these yield generally similar results, but butadiene is preferred. The Diels-Alder condensation is effected at elevated temperatures usually in the range of from about 50° to about 190° C. and at a pressure ranging from atmospheric up to about 100 atmospheres. The reaction pressure may be attained by the introduction of a substantially inert gas such as nitrogen or argon into the reaction zone, the amount of pressure which is utilized being that which is sufficient to maintain at least a portion of the reactants in the liquid phase.

The 4-chloromethylcyclohexene which has been prepared according to the above paragraph is then selectively alkylated utilizing an olefinic hydrocarbon as the alkylating agent. The selective alkylation in which the alkyl substituent is positioned on the ring rather than on the side chain is effected by treating the reactants in the presence of a free-radical generating compound and hydrogen chloride. In the preferred embodiment of the invention the olefinic hydrocarbon which is utilized as the alkylating agent will comprise an alpha-olefin containing from about 3 to about 20 carbon atoms. By utilizing an alkylation catalyst comprising a free-radical generating compound and a promoter comprising hydrogen chloride, it is possible to obtain a normal alkyl side chain on the cyclohexene ring rather than a secondary alkyl side chain which would result if the alkylation were effected in the presence of an acidic catalyst of the Friedel-Crafts type or sulfuric acid, etc. Specific examples of these olefinic hydrocarbons which are utilized as alkylating agents include 1-hexene, 1-heptene, 1-octene, 1-nonene, 1-decene, 1-undecene, 1-dodecene, 1-tridecene, 1-tetradecene, etc. It is also contemplated within the scope of this invention that other alpha-olefins containing less than 6 or more than 14 carbon atoms may also be utilized, said olefins including propene, 1-butene, 1-pentene, 1-pentadecene, 1-hexadecene, 1-heptadecene, 1-octadecene, 1-nonadecene, 1-eicosene, etc.

The catalysts which are used in this step of the invention will include peroxy compounds containing the bivalent radical —O—O— which decompose to form free radicals which initiate the general reaction and are capable of inducing the condensation of the chloromethylcyclohexene with the 1-alkene. Examples of these catalysts include the persulfates, perborates, percarbonates of ammonium and of the alkali metals or organic peroxy compounds. The organic peroxy compounds constitute a preferred class of catalysts for use in the invention and include peracetic acid, persuccinic acid, methyl ethyl ketone peroxide, methyl isobutyl ketone peroxide, acetyl peroxide, dipropionyl peroxide, di-t-butyl peroxide, butyryl peroxide, lauroyl peroxide, benzoyl peroxide, tetralin peroxide, urea peroxide, t-butyl perbenzoate, t-butyl hydroperoxide, methylcyclohexyl hydroperoxide, cumene hydroperoxide, diisopropylbenzene hydroperoxide, etc. Mixtures of peroxy compound catalysts may be employed or the peroxy compound catalyst may be utilized in admixture with various diluents. Thus, organic peroxy compounds which are compounded commercially with various diluents which may be used include benzoyl peroxide compounded with calcium sulfate, benzoyl peroxide compounded with camphor, phthalate esters, etc. Only catalytic amounts (less than stoichiometric amounts) need be used in the process.

The alkylation of the chloromethylcyclohexene with the l-alkene is effected at elevated reaction temperatures which should be at least as high as the initial decomposition temperature of the free-radical generating catalyst, such as the peroxide compound, in order to liberate and form free radicals which promote the reaction. In selecting a particular reaction temperature for use in the process of the present invention, two considerations must be taken into account. First, sufficient energy by means of heat must be supplied to the reaction so that the reactants, namely the chloromethylcyclohexene and the l-alkenes will be activated sufficiently for condensation to take place when free radicals are generated by the catalyst. Second, free-radical generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 11 hours at 125° C., 4 hours at 135° C., and 1.5 hours at 145° C. A reaction system temperature must then be selected so that the free-radical generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for condensation. When the half life of the free-radical generating catalyst is greater than 10 hours, radicals are not generated at a sufficient rate to cause the reaction of the process of the present invention to go forward at a practically useful rate. Thus the reaction temperature may be within the range of from about 50° to about 300° C., and at least as high as the decomposition temperature of the catalyst, by which is meant a temperature such that the half life of the free-radical generating catalyst is not greater than 10 hours. Since the half life for each free-radical generating catalyst is different at different temperatures, the exact temperature to be utilized in a particular reaction will vary. However, persons skilled in the art are well acquainted with the half life vs. temperature data for different free-radical generating catalysts. Thus it is within the skill of one familiar with the art to select the particular temperature needed for any particular catalyst. However, the operating temperatures generally do not exceed the decomposition temperature of the catalyst by more than about 100° C. since free-radical generating catalysts decompose rapidly under such conditions. For example, when a free-radical generating catalyst such as t-butyl perbenzoate is used, having a 50 percent decomposition temperature (in 10 hours) of approximately 105° C., the operating temperature of the process is from about 105° to about 205° C. When di-t-butyl peroxide having a 10 hour, 50 percent decomposition temperature of about 125° C. is used, the process is run at a temperature ranging from about 125° to about 225° C. Higher reaction temperatures may be employed, but little advantage is gained if the temperature is more than the hereinbefore mentioned 100° C. higher than the 10 hour, 50 percent decomposition temperature of the catalyst. The general effect of increasing the operating temperature is to accelerate the rate of condensation reaction of the chloromethylcyclohexene with the l-alkene. However, the increased rate of reaction is accompanied by certain amounts of decomposition. In addition to the elevated temperatures which are utilized, the reaction may also be effected at elevated pressures ranging from about 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment to charge the reactants and the catalyst to the vessel and to pressure the vessel with 10 or 30 or 50 or more atmospheres of an inert gas such as nitrogen. This helps to insure the presence of liquid phase conditions. However, when the mole quantity of reactants is sufficient, the pressure which they themselves generate at the temperature utilized is sufficient to maintain the desired phase conditions.

Furthermore, the concentration of the catalyst employed in this process may vary over a rather wide range but it is desirable to utilize low concentrations of catalysts such as from about 0.1 to about 10 percent of the total weight of the combined starting materials charged to the process. The reaction time may be within the range of from less than one minute to several hours, depending upon temperature and the half life of the catalyst. Generally speaking, contact times of at least 10 minutes are preferred.

In addition to the free-radical generating catalyst, the alkylation is also effected in the presence of a hydrogen chloride compound. The hydrogen chloride compound is used as a promoter for the reaction and also is used to prevent or inhibit telomerization, said telomerization being a polymerization reaction in which unwanted side reaction products may be formed. The hydrogen chloride may be present as anhydrous hydrogen chloride, as concentrated hydrochloric acid or as an aqueous solution of hydrochloric acid, the hydrochloric acid being present in an amount of from 5 to about 38 percent in said aqueous solution.

The resulting disubstituted cyclohexene comprising an n-alkyl chloromethylcyclohexene is thereafter reacted with an alkali metal salt of a sulfur-containing compound such as an alkali sulfate or alkali bisulfate. Representative examples of these alkali metal salts will include sodium sulfate, sodium bisulfate, potassium sulfate, potassium bisulfate, lithium sulfate, lithium bisulfate, rubidium sulfate, rubidium bisulfate, cesium sulfate, cesium bisulfate, etc., the preferred compounds comprising the sodium or potassium salts due to their relatively lower cost and greater availability. The reaction is usually effected at elevated temperatures in the range of from about 50° to about 150° C. or more and at atmospheric pressure. Preferably the sulfation is effected in the presence of a highly polar or high dielectric solvent, said solvents including dimethyl sulfoxide, dimethylformamide, sulfolane dioxane, ethanol, ethylene glycol, glycerol, nitromethane, etc.

The process of this invention in which the novel compositions of matter useful as biodegradable detergents are prepared may be effected in either a batch type or continuous type of operation. When a batch type operation is used, a quantity of the allyl chloride is placed in an appropriate apparatus such as an autoclave and butadiene is charged thereto. The autoclave is then heated to the desired operating temperature and pressure in the range hereinbefore set forth and maintained thereat for a predetermined residence time which may range from about 0.5 up to about 10 hours or more in duration. Upon completion of the desired residence time, heating is discontinued, the autoclave is allowed to return to room temperature, the excess pressure is vented and the reaction mixture is recovered. The 4-chloromethylcyclohexene is separated from any unreacted allyl chloride by conventional means such as distillation or any other separation means known in the art and placed in a second reaction vessel along with a free-radical generating compound and the 1-alkene which is to be utilized as the alkylating agent. In addition, a promoter comprising hydrogen chloride either in gaseous form as hydrogen chloride or in aqueous form as hydrochloric acid is added to the reactor which is thereafter heated to the desired operating temperature which, as hereinbefore set forth, is at least as high as the decomposition temperature of said free-radical generating compound. After maintaining the alkylation reaction at this temperature for a predetermined period of time, heating is discontinued, the reaction mixture is allowed to return to room temperature and the alkyl-substituted chloromethylcyclohexene is again recovered by conventional means.

The n-alkyl chloromethylcyclohexene is then reacted with an alkali metal salt of a sulfur-containing compound at elevated temperatures and in the presence of a solvent of the type hereinbefore set forth. Following the sulfation step which may take again from about 0.5 up to about 10 hours or more, heating is discontinued and the desired product is separated from the solvent by fractionation or other means and passed to storage.

It is also contemplated within the scope of this invention that the desired product may be prepared while employing a continuous type of operation. When the continuous type of operation is to be used, the starting materials comprising the allyl chloride and butadiene are continuously charged to a reactor which is maintained at the proper operating conditions of temperature and pressure. After passage through this reactor, the effluent is continuously withdrawn, subjected to a separation step whereby the unreacted allyl chloride and butadiene are separated from the chloromethylcyclohexene and recycled to form a portion of the feed stock while the latter is continuously charged to an alkylation apparatus which is also maintained at the proper operating conditions of temperature and pressure. In addition, the 1-alkene, the free-radical generating compound and the hydrogen chloride promoter are also continuously charged to this alkylation apparatus through separate lines. After completing the desired residence time in the alkylation apparatus, the reactor effluent is continuously withdrawn, again subjected to separation steps whereby unreacted starting materials, promoter, free-radical generating compound and by-products are separated from the alkyl-substituted chloromethylcyclohexene. The unreacted materials are recycled to form a portion of the feed stock to the apparatus while the alkyl-substituted chloromethylcyclohexene is continuously charged to a sulfation reactor. The alkali metal sulfur-containing compound such as sodium sulfate, sodium bisulfate, etc., is continuously charged to the sulfation reactor along with the solvent. The solvent may be charged to the reactor through a separate line or one or both of the reactants may be admixed with the solvent prior to entry into said reactor and the resulting mixture charged thereto in a single stream. After completion of the desired residence time in the sulfation reactor, the effluent is again continuously withdrawn and subjected to separation steps which are conventional in nature whereby unreacted starting material and solvent are separated from the desired compound, the latter being passed to storage while the unreacted starting materials are recycled to form a portion of the feed stock.

Some specific examples of the novel compositions of matter of the present invention which may be prepared according to the process hereinbefore set forth will include those compounds having the generic formula:

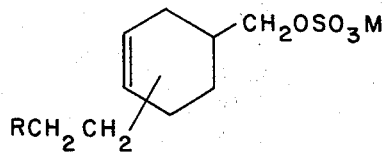

in which M is an alkali metal and R is an alkyl group of from 1 to about 14 carbon atoms such as sodium(n-propyl-3-cyclohexenyl)methano sulfate, sodium(n-butyl-3-cyclohexenyl)methano sulfate, sodium(n-pentyl-3-cyclohexenyl)methano sulfate, sodium(n-hexyl-3-cyclohexenyl)methano sulfate, sodium(n-heptyl-3-cyclohexenyl)methano sulfate, sodium(n-octyl-3-cyclohexenyl)methano sulfate, sodium(n-nonyl-3-cyclohexenyl)methano sulfate, sodium(n-decyl-3-cyclohexenyl)methano sulfate, sodium(n-undecyl-3-cyclohexenyl)methano sulfate, sodium(n-dodecyl-3-cyclohexenyl)methano sulfate, sodium(n-tridecyl-3(cyclohexenyl)methano sulfate, sodium(n-tetradecyl-3-cyclohexenyl)methano sulfate, potassium(n-propyl-3-cyclohexenyl)methano sulfate, potassium(n-pentyl-3-cyclohexenyl)methano sulfate, potassium(n-heptyl-3-cyclohexenyl)methano sulfate, potassium(n-nonyl-3-cyclohexenyl)-methano sulfate, potassium(n-undecyl-3-cyclohexenyl)methano sulfate, potassium(n-tridecyl-3-cyclohexenyl)methano sulfate, lithium(n-butyl-3-cyclohexenyl)methano sulfate, lithium(n-hexyl-3-cyclohexenyl)methano sulfate, lithium(n-octyl-3-cyclohexenyl)methano sulfate, lithium(n-decyl-3-cyclohexenyl)methano sulfate, lithium(n-dodecyl-3-cyclohexenyl)methano sulfate, lithium(n-tetradecyl-3-cyclohexenyl)methano sulfate, etc. It is to be understood that the aforementioned biodegradable detergents are only representative of the novel class of compounds and that the present invention is not necessarily limited thereto.

The following examples are given to illustrate the process of the present invention which, however, are not intended to limit the generally broad scope of the present invention in strict accordance therewith.

EXAMPLE I

In this example a mole proportion of allyl chloride is placed in the glass liner of a rotating autoclave. The autoclave is sealed, a mole proportion of butadiene along with a sufficient amount of nitrogen is pressed in until an initial operating pressure of 30 atmospheres is reached. The autoclave and contents thereof are then heated to a temperature of 130° C. and maintained in a range of 130° to 140° C. for a period of 4 hours. At the end of the 4-hour period, heating is discontinued, the autoclave is allowed to return to room temperature and the excess pressure is discharged therefrom. The autoclave is opened and the reaction mixture is recovered and subjected to fractional distillation under reduced pressure whereby the desired product comprising 4-chloromethylcyclohexene is separated and recovered.

The aforementioned 4-chloromethylcyclohexene which is prepared according to the above paragraph is then placed in another liner of a rotating autoclave along with 1-tetradecene, the chloromethylcyclohexene being present in a molar excess over the tetradecene. In addition, a catalyst comprising di-t-butyl peroxide and a promoter comprising concentrated hydrochloric acid is also added to the liner. The liner is then sealed into the autoclave and nitrogen is pressed in until an initial operating pressure of 30 atmospheres is reached. The autoclave and contents thereof are then heated to a temperature of 130° C. and maintained in a range of from 130° to 140° C. for a period of 8 hours. At the end of the 8-hour period, heating is discontinued, the autoclave is allowed to return to room temperature, the excess pressure is discharged and the autoclave is opened. The reaction mixture is subjected to fractional distillation under reduced pressure whereby the desired n-tetradecyl-3-cyclohexenylmethyl chloride is recovered.

The disubstituted cyclohexene is reacted in a molar proportion with sodium sulfate, said reaction being effected in the presence of a solvent comprising dimethyl sulfoxide at a temperature of about 60° C. for a period of 4 hours. At the end of the 4-hour period, heating is discontinued, the reaction mixture is again subjected to fractional distillation under reduced pressure whereby the desired product comprising sodium(n-tetradecyl-3-cyclohexenyl)methano sulfate is recovered.

EXAMPLE II

In a manner similar to that set forth in Example I above, 76.5 grams (1.0 mole) of allyl chloride is placed in the glass liner of a rotating autoclave. The liner is sealed into the autoclave and 54 grams (1.0 mole) of butadiene is charged thereto. The autoclave is then heated to a temperature of 125° C. and maintained thereat for a period of 4 hours. At the end of this time, heating is discontinued and the autoclave is allowed to return to room temperature. The autoclave is opened and the reaction mixture is recovered therefrom. Following this, the mixture is subjected to fractional distillation whereby the desired product comprising 4-chloromethylcyclohexene is separated from any unreacted allyl chloride and recovered.

The 4-chloromethylcyclohexene which is prepared according to the above paragraph is then placed in the glass liner of a rotating autoclave along with 1-octene, the charge stock usually consisting of a molar excess of the chloromethylcyclohexene over the 1-octene in a range of from about 1.5:1 to about 2:1 moles of chloromethylcyclohexene per mole of 1-octene. In addition, 7 grams of di-t-butyl peroxide and 20 grams of concentrated hydrochloric acid are placed in the autoclave. The autoclave is sealed and nitrogen is pressed in until an initial operating pressure of 30 atmospheres is reached. The autoclave and contents thereof are then heated to a temperature of 130° C. and maintained thereat for a period of 8 hours. At the end of the 8-hour period, heating is discontinued, the autoclave is allowed to return to room temperature and the excess pressure is discharged therefrom. The autoclave is opened, the reaction mixture is recovered and subjected to fractional distillation, usually under reduced pressure, whereby the desired product comprising n-octyl-3-cyclohexenylmethyl chloride is recovered.

The n-octyl-3-cyclohexenylmethyl chloride which is prepared according to the above paragraph is then sulfated by placing said compound in a flask along with an equimolar amount of sodium sulfate and a solvent comprising dimethyl sulfoxide. The flask is then heated to a temperature of 50° C. and the reaction mixture is maintained at this temperature for a period of 4 hours, at the end of which time, heating is discontinued. Upon cooling, the reaction mixture is separated from the dimethyl sulfoxide solvent and any unreacted starting materials, the desired product comprising sodium(n-octyl-3-cyclohexenyl)methano sulfate being recovered therefrom.

EXAMPLE III

In this example 4-chloromethylcyclohexene is prepared in a manner similar to that set forth in Examples I and II above. Thereafter the 4-chloromethylcyclohexene is placed in the glass liner of a rotating autoclave along with 1-decene, a catalyst comprising di-t-butyl peroxide and concentrated hydrochloric acid, the 4-chloromethylcyclohexene being in a molar excess over the 1-decene. The autoclave is sealed, nitrogen is pressed in until an initial operating pressure of 30 atmospheres is reached, after which the autoclave is heated to a temperature of 130° C. and maintained in a range of from 130° to 140° C. for a period of 8 hours. At the end of this time, heating is discontinued, the autoclave is allowed to return to room temperature and the excess pressure is discharged therefrom. The autoclave is opened, the reaction mixture is recovered and subjected to conventional means of separation whereby the n-decyl-substituted chloromethylcyclohexene is separated and recovered.

The n-decyl-substituted chloromethylcyclohexene is then treated in a manner similar to that hereinbefore set forth with potassium sulfate at a temperature of about 60° C. in the presence of a solvent comprising ethanol, said reaction being effected for a period of 4 hours. At the end of the 4-hour period, heating is discontinued, the mixture is recovered and subjected to conventional means of separation whereby the desired product comprising potassium(n-decyl-3-cyclohexenyl)methano sulfate is separated and recovered.

EXAMPLE IV

In this example 4-chloromethylcyclohexene is prepared in a manner similar to that hereinbefore set forth by condensing butadiene and allyl chloride in a Diels-Alder manner. Following the preparation and recovery of the 4-chloromethylcyclohexene, it is then placed in an alkylation apparatus along with 1-dodecene, benzoyl peroxide and concentrated hydrochloric acid, the alkylation being effected at a temperature in the range of about 80° to 85° C. for a period of 4 hours. At the end of the 4-hour period, heating is discontinued, the reactor is allowed to return to room temperature and the reaction mixture is recovered therefrom. After subjecting the reaction mixture to fractional distillation, the desired product comprising n-dodecyl-3-chloromethylcyclohexene is recovered. This product is then reacted with sodium sulfate at a temperature of about 75° C. for a period of 4 hours in the presence of a 1,4-dioxane solvent. At the end of the 4-hour period, heating is again discontinued and the reaction mixture is allowed to cool to room temperature. After cooling to room temperature, the mixture is subjected to conventional means of separation whereby the desired product comprising sodium(n-dodecyl-3-cyclohexenyl)-methano sulfate is recovered.

EXAMPLE V

To the glass liner of a rotating autoclave is charged 76.5 grams (1.0 mole) of allyl chloride and thereafter the liner is sealed into the autoclave. Following this, 54 grams (1.0 mole) of butadiene is charged thereto and the autoclave is heated to a temperature of 125° C. After maintaining the autoclave at this temperature for a period of 4 hours, heating is discontinued and the autoclave is allowed to return to room temperature. The autoclave is opened and the reaction mixture is subjected to fractional distillation whereby the desired 4-chloromethylcyclohexene is separated from any unreacted allyl chloride and recovered.

The 4-chloromethylcyclohexene which is thus prepared is placed in the glass liner of a rotating autoclave along with l-octene, said chloromethylcyclohexene being in a molar excess over the l-octene. In addition to the starting materials, 7 grams of di-t-butyl peroxide and 20 grams of concentrated hydrochloric acid are also placed in the autoclave which is thereafter sealed and pressured to an initial operating pressure of 30 atmospheres with nitrogen. The autoclave and contents thereof are then heated to a temperature of 130° C. and maintained thereat for a period of 8 hours, at the end of which time heating is discontinued and the autoclave is allowed to return to room temperature. The excess pressure is discharged, the autoclave is opened and the reaction mixture which is recovered therefrom is subjected to fractional distillation under reduced pressure to separate and recover n-octyl-3-cyclohexenylmethyl chloride.

The aforementioned n-octyl-3-cyclohexenylmethyl chloride is sulfated by treating the compound with an equimolar amount of potassium sulfate in the presence of a solvent comprising dimethyl sulfoxide, the reaction being effected at a temperature of 50° C. for a period of 4 hours. At the end of the 4-hour period, the reaction mixture is treated in a manner similar to that hereinbefore set forth whereby the desired product comprising potassium(n-octyl-3-cyclohexenyl)methano sulfate is separated and recovered.

I claim as my Invention:

1. A biodegradable detergent compound of the formula:

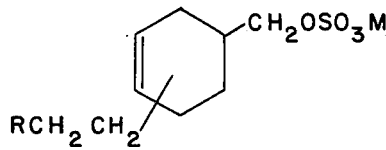

in which M is an alkali metal and R is an alkyl group of from 1 to about 14 carbon atoms.

2. The biodegradable detergent compound of claim 1 being sodium(n-octyl-3-cyclohexenyl)methano sulfate.

3. The biodegradable detergent compound of claim 1 being sodium(n-tetradecyl-3-cyclohexenyl)methano sulfate.

4. The biodegradable detergent compound of claim 1 being potassium(n-decyl-3-cyclohexenyl)methano sulfate.

5. The biodegradable detergent compound of claim 1 being sodium(n-dodecyl-3-cyclohexenyl)methano sulfate.

6. The biodegradable detergent compound of claim 1 being potassium(n-octyl-3-cyclohexenyl)methano sulfate.

* * * * *